United States Patent [19]

Evans et al.

[11] Patent Number: 5,292,499

[45] Date of Patent: Mar. 8, 1994

[54] METHOD OF PREPARING MEDICAL AEROSOL FORMULATIONS INCLUDING DRUG DISSOLVED IN REVERSE MICELLES

[75] Inventors: Richard M. Evans, Norwood, Mass.; Stephen J. Farr, Cardiff, Wales

[73] Assignee: University of Wales College of Cardiff, Cardiff, United Kingdom

[21] Appl. No.: 828,195

[22] Filed: Jan. 30, 1992

Related U.S. Application Data

[63] Continuation of Ser. No. 580,926, Sep. 11, 1990, abandoned.

[51] Int. Cl.$^5$ .............................................. A61K 9/12
[52] U.S. Cl. ................................... 424/45; 424/43; 424/450; 514/937
[58] Field of Search ....................... 424/45, 43, 450

[56] References Cited

U.S. PATENT DOCUMENTS 4,814,161  3/1989  Jinks ........................... 424/45
5,230,884  7/1993  Evans et al. ................. 424/45

FOREIGN PATENT DOCUMENTS 372777  6/1990  European Pat. Off. .

OTHER PUBLICATIONS

P. L. Luisi et al. (1988). Biochimica et Biophysica Acta, vol. 947, PP 209–246.
Byron, P. R. (1990). Respiratory Drug Delivery. CRC Press, Inc., pp. 249–257.
Evans, R. M. et al. (1988). Journal of Pharmaccy & Pharmacology, vol. 40, p. 7P.

Primary Examiner—Thurman K. Page
Assistant Examiner—Raj Bawa
Attorney, Agent, or Firm—Whitham & Marhoefer

[57] ABSTRACT

The present invention provides a method for the production of medicinal aerosol compositions which are made up of a homogenous solution of aerosol propellants, a surfactant and a pharmaceutically active compound, where the process comprises purifying the surfactant, removing the water from the surfactant, and dispersing the surfactant in an aerosol propellant with a hydrophilic pharmaceutical composition and a controlled amount of water. The present invention also provides medicinal aerosol compositions produced by this method which are a homogenous solution of the pharmaceutically active compound contained in reverse micelles made up of the surfactant; and methods of using the medicinal aerosols to provide an effective amount of a therapeutic agent.

31 Claims, 3 Drawing Sheets

METHOD OF PREPARING MEDICAL AEROSOL FORMULATIONS INCLUDING DRUG DISSOLVED IN REVERSE MICELLES

This application is a continuation of Ser. No. 07/580,926, filed Sep. 11, 1990 and now abandoned.

TECHNICAL FIELD

The present invention relates generally to medicinal pressure pack formulations and to a method of preparing and using such products. More specifically, the present invention relates to a reverse micelle colloidal dispersion of hydrophilic pharmaceutically active compounds prepared with aerosol propellant formulations. These drug containing CFC aerosol propellant formulations are useful for topical or for endopulmonary or nasal inhalation administration.

BACKGROUND OF THE INVENTION

Since the 1950's, the delivery of locally acting medicaments to the respiratory tract, in the treatment of the reversible component of an obstructive airways disease, has largely involved administration using the metered dose inhaler (MDI). Over the last twenty years, the range of drugs administered by inhalation has increased to include: bronchodilators, corticosteroids, anticholinergics, the prophylactic agents sodium cromoglycate and nedocromil sodium.

Further, the art teaches the use of aerosol propellants as a method of obtaining local anesthesia in the bronchial airways using lignocaine aerosol and the administration of nebulized morphine to relieve dyspnea.

Metered dose inhalers (MDI's), formulated as suspensions of a micronised drug in a chlorofluorocarbon (CFC) formulation, represent a major device for the delivery of locally active drugs used in the treatment of respiratory disorders and are well known in the art. Despite the identification and optimization of the major parameters which influence the performance of MDI's such as particle size, vapor pressure, and surfactant concentration (Poli et al., M. H. J. Pharm. Sci., 58 (1969) 484), their use in practice results in extensive extrapulmonary deposition with frequently less than 10 percent of the metered dose actually reaching the targeted site.

In the past, metered dose inhalers (MDI's) formulations have been heterogeneous systems which require redispersion prior to use of the medicinal aerosol. These formulations suffer from the drawback that they are prone to agglomeration of the finely divided drug particles, which can lead to the formation of 'cakes'. Further, low levels of solubility may be manifested as crystal growth which can lead to changes in the size distribution of the suspended solid. Either of these phenomena can result in inadequate delivery of the desired amount of the drug.

The present invention seeks to overcome these problems of prior art aerosol systems through the formulation of a homogeneous colloidal dispersion system in contrast to both heterogeneous (suspension) systems and homogenous systems which include co-solvents such as ethanol.

Pharmaceutical pressurized pack dosage forms contain the therapeutically active ingredient dissolved or suspended in a propellant system which is capable of expelling the contents of the pack through an opened valve. For potent drugs, such as those used in the treatment of bronchial asthma, the valve includes a metering device that delivers a measured volume typically in the range of 25–100 μL. The prior art inhalation packs also contain a small percentage of surfactant which acts as a suspending agent, and, to a lesser extent, as a lubricant for the metering valve assembly.

Prior art solutions also generally included a high boiling point co-solvent, such as ethanol, which is miscible with the chlorofluorocarbon formulation. These were even more inefficient than present day devices because they decreased the rate of evaporation of propellant from the aerosol droplets.

Inhalation devices offer the advantage of delivering drugs directly to the required site of action and in doing so, avoid 'systemic' first-pass metabolism. Pulmonary first-pass metabolism may occur, but the activity of enzymes found in the lungs is generally lower than corresponding enzymes in the liver. The amount of drug required to bring about a pharmacological response can be much smaller than that required when the drug is administered by another route, and thus, the incidence and severity of any potential side-effects can also be reduced. Furthermore, for compounds with rapid absorption, local action can be immediate, and the potential of systemic delivery also exists.

As a result of a combination of factors in the administration process, the release of a large and rapidly moving aerosol bolus and the physical constraints of the tracheabronchial tree, the majority of the metered dose for an MDI fails to reach the intended site of action, mainly through deposition in the orapharyngeal region. This means that while the pharmacological response is efficacious, the administration of the drug is brought about in an inefficient manner. Typically, a loss of drug of between 80 to 90 percent is often encountered which, provided the required pharmacological response occurs, is of little concern in the case of compounds with few localized side-effects and for those which are inactivated in the GI tract. However, with corticosteroids, deposition in the oropharynx can result in fungal overgrowth due to the immunosuppressive side effects of these compounds.

For pressurized packs used under optimal conditions, only some 10–14 percent of the metered dose is deposited in the bronchial tree. Deposition can be improved by using a spacer in conjunction with the MDI and increases to around 15 percent with the Nebuhaler® and Inspir Ease® devices. In separate research using an open spacer, Newman and co-workers demonstrated an increase in dose reaching the lung from 11 percent to between 13 and 16 percent (depending on breathing pattern) for an Intal® inhaler.

U.S. Pat. No. 4,814,161 to Jinks et al. discloses the existence of reverse micellization and the self association of non-ionic surfactants in apolar media. Jinks et al. discloses a technique for incorporating drugs into chlorofluorocarbon aerosol propellants with the addition of a co-solvent, such as ethanol. Jinks et al. does not disclose the exclusion of moisture associated with the surfactant prior to formulation in order to prevent phase separation, which is produced by excess water. Jinks et al. further does not teach the manipulation of the water pool through the addition of water to make it more or less suitable as a site for solubilization.

Amphiphatic molecules in apolar media may associate into reversed or inverted micellar solutions (Luisi et al, Biochim. Biophysi. Acta, 947 (1988) 209) which are homogeneous and optically transparent and have the ability to solubilize quantities of water. The result of incorporating water into such systems is the production of a water-pool and the formation of swollen micelles, which serve as centers for the solubilization of drugs of various physico-chemical characteristics.

The use of therapeutic concentrations of a model bronchodilator solubilized in heterogeneous systems is disclosed in an article, Evans et al, "Surfactant Association and Water Uptake in a Model Chlorofluorocarbon System," J. Pharm. Pharmacol., 39 (1988) 7P. This article discusses the potential for solubilizing drugs through the alteration of the size and polarity of reverse micelle structure.

SUMMARY OF THE INVENTION

The present invention relates to medicinal aerosol products. More specifically, the present invention relates to a medicinal aerosol composition comprising a homogenous solution phase system which contains a hydrophilic pharmaceutically active compound in a controlled reverse micelle, a process for forming the aerosol composition, and a method of using the aerosol composition.

One aspect of the present invention is a method of solubilizing pharmaceutically active hydrophilic compounds within a propellant system. This method comprises the steps of a) purifying a surfactant system, b) reducing the water associated with the surfactant system to an acceptable level, and c) formulating the surfactant system into a homogeneous reverse micelle containing propellant system by adding the propellant, an amount of water sufficient to provide the desired shape and polarity of the micelle, and a hydrophilic pharmaceutically active agent.

A second aspect of the present invention is an aerosol composition comprising a solution of one or more aerosol propellants, a surfactant and a pharmaceutically active compound. The surfactant used in the above-mentioned aerosol composition forms reverse micelles and the pharmaceutically active compound is a hydrophilic compound associated with the reverse micelles.

Another aspect of the present invention is a method of treatment comprising the use of a formulation comprising an aerosol propellant blend, a surfactant and a pharmaceutically active compound to introduce effective amounts of the solubilized hydrophilic pharmaceutically active agent into the respiratory tract of a patient, or to deliver these topically for local or systemic action.

DETAILED DESCRIPTION OF THE PREFERRED EMBODIMENTS

The present invention relates to a formulation for incorporating hydrophilic drugs into aerosol propellants, a process for making said formulation and a method of using said formulation.

Therefore, one aspect of the present invention provides a method of solubilizing potent medicinally active compounds within metered dose inhaler (MDI) propellant systems through the formulation of a homogeneous, solution phase system. This method for the production of solution systems preferably does not include co-solvents, since co-solvents adversely affect the dose accuracy and the propellant evaporation. However, small amounts of a polar co-solvent, such as ethanol, may be incorporated if desired.

A second aspect of the present invention relates to an aerosol composition which comprises a propellant, and a hydrophilic pharmaceutically effective agent which has been solubilized in a reverse micelle.

An additional aspect of the present invention relates to the use of the compositions of the present invention in a therapeutic manner to introduce an effective amount of a pharmaceutically acceptable compound into the respiratory tract. More specifically, one embodiment of the present invention provides a process for forming homogenous solution phase aerosol compositions which are suitable for use within a measured dose inhaler. This method comprises the steps of purifying the surfactant, drying the surfactant to remove water, and forming the reverse micelles through the addition of the pharmaceutically active agent, the chlorofluorocarbon solvent, and a controlled amount of water to control the size and shape of the pharmaceutical containing micelles.

A preferred embodiment of this process is described as follows.

The first step of the method of preparation is the purification of the surfactants which are suitable for use in forming the reverse micelles. It is generally advantageous for the reverse micelles of the present invention to utilize pure surfactant(s) and in the event of the non-availability of a pure source(s) of the required surfactant(s), a purification step would be required.

Conventional methods for purification of surfactants are suitable for use in this purification step. Such methods are well known to those skilled in the art. A particularly preferred method is column chromatography on aluminum oxide (neutral) using a chloroform/methanol mixture as an eluant.

The second step of this present invention's method is the reduction of moisture associated with the surfactant prior to the formation of the solution phase system to an acceptable level. The acceptable level of water which is associated with the surfactant after drying should be in the range of $R=0.5$ to the limit of water solubility which does not cause phase separation, where "R" is defined as the ratio of the moles of water to moles of surfactant. This upper limit is individually established for the particular system. A preferred range for the acceptable level of water is the range of $R=0.5$ to $R=1$.

Elimination of water which is associated with the surfactants provides several advantages to the present invention. First, it prevents phase separation of the final composition, which is produced by the excess water. In addition, the reduction of water allows precise control of the amount of water in the final system. This is important because the shape and characteristics of the final reverse micelles can be controlled and altered by the addition of water in small, carefully controlled increments. Such control over the size and shape of the reverse micelles allows each system to be specifically transferred to a particular drug. Thus, allowing one skilled in the art to optimize drug solubilization such that a therapeutically active amount of drug can be administered to a patient.

A preferred method for removing the water comprises heating dried methanol and using it to wash the surfactant. Following the washing period, the solvent is evaporated. This process is repeated three times, each time drying to constant weight.

An alternative drying method which is suitable for use to remove the water from the surfactant is freeze drying.

The third step of this embodiment of the present invention is to take the dried and purified surfactant(s) and formulate it into aerosol compositions suitable for use in pressurized pack systems. These aerosol compositions are solutions of one or more propellants which contain the required concentration of surfactant(s) and the desired level of solubilized water, both of which are optimized for the desired hydrophilic pharmaceutically active agent. The ingredients are combined in any convenient manner and are then placed into an appropriate storage container or delivery device.

The propellants may be chilled to below ambient temperature for filling. A preferred temperature range for is in the range 0° to 24° C. A particularly preferred temperature range is 4° to 15° C. A most preferred range is 4° to 10° C.

The system should be allowed to equilibrate between 2 and 24 hours. A more preferred equilibration time for many systems is between 4 and 12 hours. A particularly preferred equilibration time is between 5 and 10 hours. Effective equilibration is required before colloidal dispersion can be therapeutically administered. The resulting composition is essentially homogeneous in nature, unlike the suspensions disclosed in the cited art, and, as a result, avoids the problems of the prior art aerosol composition.

The present invention further relates to the inclusion of water, and a pharmaceutically active compound which forms a ternary phase system, and leads to the formation of reverse micelles, the cores of which act as centers for the solubilization of the drug.

More specifically, this embodiment of the present invention relates to the manipulation of the water pool through the addition of water solubilized in the reverse micelle system which allows the shape and core polarity to be manipulated in such a way as to make it more or less suitable as a site for the solubilization of drug molecules.

The solubility of the hydrophilic pharmaceutically acceptable agent is controlled by the relative amounts of water and surfactant which are added to the chlorofluorocarbon solution. To accomplish this optimization, the core polarity of the reverse micelles is manipulated by the addition of an appropriate amount of water. This allows solubilization of a variety of drug molecules which possess varying physico-chemical characteristics.

Surfactant concentration depends upon the potency of the active compound to be administered by the nasal, pulmonary or transdermal route, the solubility of the surfactant in the propellant blend and the affect of solubilizing water into the system (if required). Each of these variables will influence the spray characteristics and hence droplet size of the aerosol generated from such packs.

A minimum surfactant concentration will depend upon the operational critical micelles concentration (CMC) of that surfactant since without micelle formulation active compounds will not be solubilized. The surfactant concentration should be between 0.05% and 2% w/v. A preferred range is between 0.25% to 2% w/v. A particularly preferred range is between 0 5% and 2% w/v.

The upper limit for water concentration in the present compositions is limited by the amount which will cause phase separation. This amount is determined from the ternary phase diagram which may be constructed for each system and which is well within the ordinary skill of the art. The preferred amount of water is that which will render the micellar core polarity optimal for drug solubilization.

The water concentration in the present composition is dependent on the amount of surfactant present in solution. The R value should be in the range of $R=1$ to $R=20$. A preferred range for "R" is the range $R=1$ to $R=16$. A particularly preferred range is the range $R=1$ to $R=5$.

The exact size of reverse micelles will vary for surfactant/water combination. Changes in the sizes of the micelles can be readily determined by one skilled in the art using light scattering and spectrophotometric techniques.

An additional embodiment of the present invention is the aerosol solution itself which is formed by the above referenced process. This aerosol composition is a colloidal dispersion system comprising a propellant containing reverse micelles made from the surfactant, and where the reverse micelles contain a hydrophilic pharmaceutically active agent.

The solution phases of the present invention are homogenous solution phases, unlike the emulsions and suspensions of the prior art. As a result, they avoid the caking, clogging, and crystallization problems which occur in the use of suspension-based aerosol systems.

A further embodiment of the present invention is the use of an aerosol composition of the present invention to provide a therapeutically effective amount of a desired hydrophilic pharmaceutically acceptable compound to the respiratory tract of a patient. The solution phase system should minimize the efficiency problems observed in the prior art and provide a greater efficiency in providing therapeutic levels of the active agent to the patient.

The aerosol compositions of the present invention are suitable for use in the formulation of pressure pack systems. They are particularly well suited for use in metered dose inhaler systems.

Suitable surfactants for use in the present invention for forming the reverse micelles include a variety of glycerol phosphatides, including: phosphatidyl choline (lecithin), phosphatidyl ethanolamine (cephalin), phosphatidyl inositol, phosphatidyl serine, diphosphatidyl glycerol, sorbitan mono- and tri-oleates (Span 80 and 85), diolein (DO), oleic acid (OA) or phosphatidic acid.

Preferred surfactants are sorbitan mono- and tri-oleates (Span 80 and 85), diolein (DO), oleic acid (OA) and purified phosphatidyl choline (PC).

A particularly preferred surfactant is phosphatidyl choline which has been purified from the lecithin of soya oil (Epikuron 200) using column chromatography on aluminum oxide (neutral). Suitable propellants for use in the present invention include either alone or in combination: n-butane (A17), isobutane (A31), perfluoropentane (PP50), trichlorofluoromethane (P11), dichlorotetrafluoroethane (P114), dichlorotrifluoroethane (P123), dichlorofluoroethane (P141b) with dichlorodifluoromethane (P12), tetrafluoroethane (P134a), propane (A108), dimethylether (DME), perfluoropropane (PP30) and heptafluoropropane (P227).

Hydrophilic pharmaceutical compositions which are suitable for use in the methods and compositions of the present invention include the following: Steroids, such as, beclomethasone dipropionate, betomethasone dipropionate, acetate, valerate, and free alcohols thereof, atropine base, prednisolone, formioterol base, hydrochlorine, fumarate and hemisulphate; Anorectics, including, chlorphentermine hydrochloride, benzphetamine hydrochloride; medically active peptides such as enkephalins, human growth factor hormone (HGH) and insulin; anti-depressants, including, imipramine hydrochloride, amitriptyline hydrochloride; anti-hypertensive agents, for example, clonidine hydrochloride; anti-neoplastic agents, for example, actinomycin C; anti-cholinergic agents, such as atropine base; dopaminergic agents, for example, bromocriptine mesylate; narcotic analgesics, including, buprenorphine hydrochloride; beta-adrenergic blocking agents, for example, propranolol hydrochloride; corticosteroids, for example, lacicortone, hydrocortisone, fluocinolone acetonide, triamanolone acetonide; prostaglandins, for example, dinoprost trometanol; sympathomimetics, for example, xylometazoline hydrochloride; tranquilizers, including, diazepam, lorazepam; Vitamins, for example, folic acid, micotinamide; bronchodilators, for example, clenbuterol hydrochloride bitolterol mesylate; and Sex Hormones, for example, ethinyloestradiol, levonorgestrel.

The hydrophilic pharmaceutical compounds suitable for use in the present invention are intended as non-limiting examples. It is well within the skill of the art to adapt the aerosol system of the present invention to include the use of hydrophilic pharmaceutically effective agents other than those listed above, and such use is within the intended scope of the present invention.

Particularly preferred drug compositions are the base and sulphate form of salbutamol in a homogeneous reverse micelle formulation in an aerosol propellant as is discussed below in the Examples section. Salbutamol is often referred to as albuterol.

It is clear that a flexibility exists within these systems to adjust the formulations of the present invention so as to optimize the dose requirements of the drug to the capacity of the system.

One potential application for the systems of the present invention is the formulation of pressure packs containing drugs which exert their effect at very low concentrations. This is because the formulation of stable low drug suspension systems would be difficult.

The exact size of reverse micelles will vary for surfactant/water combination, but Table 1 below indicates the changes that were seen to occur for a soya lecithin/P113 system which was examined using a cohort of light scattering and spectrophotometric techniques.

TABLE 1

SPECTROPHOTOMETRIC DATA FOR DRUG FORMULATIONS CONTAINING VARYING LEVELS OF SOYA LECITHIN/P113

| Moles H$_2$O moles lecithin | Molar Mass M*10$^{-6}$ | D$_0$[1] m$^2$s$^{-1}$* 10$^{11}$ | Intrinsic viscosity [η] | Ellipsoid shape | Axial[2] ratio nm | Length[3] a | δ[4] |
|---|---|---|---|---|---|---|---|
| 0.90 | 1.38 | 6.51 | 3.97 | oblate | 1.41 | 3.87 | 0.82 |
| 1.75 | 1.17 | 6.63 | 4.40 | oblate | 1.40 | 3.82 | 1.08 |
| 2.61 | 1.30 | 6.83 | 2.78 | sphere | 1.00 | 4.70 | 1.33 |
| 3.46 | 1.92 | 6.72 | 8.56 | prolate | 0.45 | 7.69 | 2.60 |
| 4.32 | 3.45 | 6.18 | 28.01 | prolate | 0.13 | 14.45 | 2.76 |
| 5.17 | 3.19 | 5.91 | 79.70 | prolate | 0.07 | 18.34 | 3.69 |

[1] Diffusion Coefficient (D$_0$) measured by photon correlation spectroscopy
[2] Axial ratio of the length to the width
[3] Length of the reverse micelle in nanometers
[4] grams solvent/grams solute The table summarizes the data obtained by the combination of spectroscopic and viscometric techniques. They should be treated with a certain degree of caution in view of the possible range of micellar sizes in the solutions. The table does, however, indicate a clear change of micellar shape; oblate for systems with R<2.6 through to spherical and finally prolate in systems with R>2.6. A significant decrease in the axial ratio of the micelles is observed as the amount of solubilized water was increased. Intermicellar interactions between these asymmetric micelles would be expected to increase with the increase of solution concentration. It should be noted that, despite the pronounced asymmetry of the micelles, the maximum dimension is less than 1/20th of the wavelength of the incident light. Consequently the observed lack of any significant dissymmetry of the scattering envelope would be anticipated.

Similar changes in micellar shape and asymmetry have been reported for several other surfactants in non-aqueous solvents following the solubilization of water (Luisi et al, 1988) and are responsible for the high viscosity exhibited by such systems in high concentration. In contrast, Kumar et al (J. Colloid Interface Sci., 99 (1984) 315) reported the formation of spherical micelles in lecithin/water/carbon tetrachloride and benzene systems. Dissymmetry values ranging from 1.6 to 2.3 were obtained, which were considered indicative of large spherical micelles of dimensions greater than 1/20th wavelength of incident light. The actual radii of these micelles were approximated to 50 nm which may be more accurately ascribed to the structure of microemulsions rather than discrete micelles. Dissymmetry, however, was described in lecithin/water/cyclohexane systems above R-6 due to the formation of elongated aggregates.

The following examples are intended to exemplify the operation of the present invention but not to limit its scope.

EXAMPLE 1

Purification of Surfactant

A large chromatography column (60 cm × 2.5 cm i.d.) was secured in a vertical position and half filled with chloroform. Aluminum oxide, neutral was poured slowly into the chloroform, while the column was tapped gently to facilitate even packing, until a column of approximately two thirds the length of the tube had formed.

After draining excess chloroform, 10 g of egg or soya lecithin, dissolved in a small volume of chloroform, was placed on top of the alumina and allowed to enter the column. Lecithin, as pure phosphatidylcholine, PC, was selectively eluted with chloroform:methanol 3:1.

Then, 50 $\mu$l aliquots of the 3:1 fractions were chromatographed on silica gel plates (Polygram sil-N-HR; Camlab, UK) in a mobile phase of chloroform:methanol:water, 14:6:1. The plates were developed by spraying with a 5 percent w/w ethanolic solution of phosphomolybdic acid and maintained at 110° C. for approximately 10 minutes.

Pure fractions, determined by the presence of a single spot ($R_f$=0.55), were pooled and evaporated to dryness using a rotary vacuum evaporator (Büchi, Switzerland) at 45° C.

Recrystallization of PC was facilitated by redissolving in the smallest volume of warm butane-1-one and adding acetone drop-wise to the solution. The pure PC was stored under acetone at −20° C. until required.

EXAMPLE 2

Formation of a Pressurized Pack System

Having purified a sufficient quantity of surfactant(s), it is then necessary to eliminate extraneous water prior to the formulation of both "dry" and swollen reverse micelle systems:

Specially dried, commercially available methanol was heated, on an electric mantle to 60° C., in a round bottomed flask containing porcelain pieces. Using 25 ml aliquots, 10 g samples of surfactant were washed in a manner similar to that outlined by van Mil et al. (J. Colloid Interface Sci., 98 (1984) 61). Following the washing period, the solvent was evaporated using a rotary vacuum evaporator (Büchi, Switzerland) at 60° C. and the process was repeated three times, each time drying to constant weight.

Absolute water content determinations were made using a Kari-Fischer Titrator AF5 (Baird and Tatlock, UK) in accordance with the manufacturer's directions. A vessel containing the test solution was placed on a balance that interfaced directly with the titration vessel, the flask replaced on the balance and the difference in the two weights recorded. The titration then proceeded automatically and the water content of the sample determined (% w/w).

EXAMPLE 3

Preparation of a Solubilized Drug System

A dried and purified surfactant was formulated into 15 mls of a pressurized pack system containing the required concentration of surfactant to provide a concentration of 0.5% w/v. 0.075 gm of soya lecithin was placed in a plastic coated glass bottle which had been previously washed, dried and stored in a desiccator containing silica gel.

Then 0.003 gm of water, which is 3 $\mu$l of water was added, using a 20 $\mu$l air displacement precision pipette (Gilson, UK). P11, at 4° C., was added drop-wise to an excess weight and allowed to evaporate until to a weight of 6.12 gm remained, facilitating evacuation of air from within the bottle. A 50 $\mu$l metering valve (Neotechnic Engineering Ltd., UK) was crimped quickly into position and 14.27 gm of P12 filled by the pressure method (Sanders, P.A. Handbook of Aerosol Technology. Van Nostrand Reinhold, N.Y., 1979). The crimping and filling procedures were conducted on a Pamasol 2005 Small Scale Crimper and Pressure Filler (Pamasol Willi Mäder AG, Switzerland) correctly adjusted for glass bottles with 20 mm diameter valves.

EXAMPLE 4

Drug Solubility in Model Surfactant/Propellant System

Surfactant solutions made from 2% w/v solution purified/dried lecithin in P113 (model propellant) containing a range of solubilized water were prepared in small conical flasks. Water was added in the range R=1 to R=5. The flasks were stoppered and sealed with Nescofilm and allowed to equilibrate for a 24 h period. After this time, excess drug was added to individual flasks, which were resealed and left for one week. During both the initial and final equilibrium periods, the flasks were stored in a shaking water bath (Grant, UK) maintained at 25±0.1° C. Prior to addition to the flasks, the drug compounds were dried in a vacuum oven and placed in a vacuum desiccator over calcium chloride for 48 hours, to minimize the entry of additional water into the systems.

Figure 1:
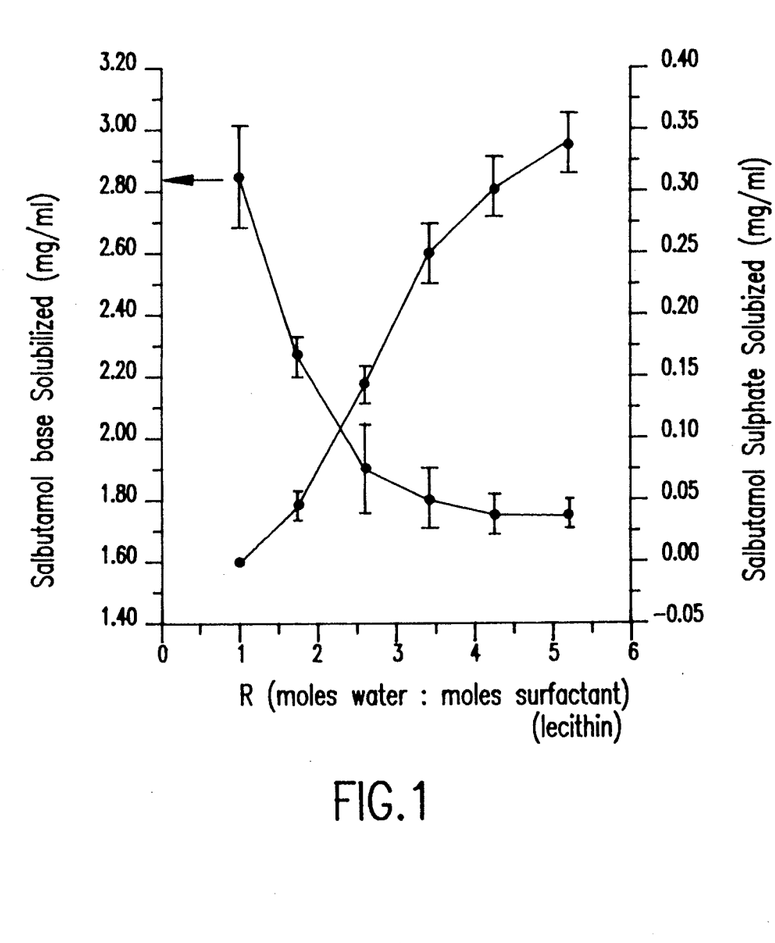
FIG. 1 is a graph showing the solubility of salbutamol in its base and salt forms in a model surfactant/propellant system at various molar ratios of water to surfactant.

At the end of the seven day period, the flasks were carefully opened and the contents were filtered through a 0.1 $\mu$m cellulose acetate/nitrate filter (25 mm, Millipore) using a microbiological clearing assembly that fit onto a 20 ml glass syringe via a lower fitting. Small additional volumes of P113 wre used to wash through t he filter and adjust for the small losses of P113 which had occurred in storage despite the use of ground glass flasks and Nescofilm. Drug solubility, in the filtrate, was assessed using photometric assay procedures. The results of these assays are displayed in FIG. 1.

Drug solubilization limits (based on these preliminary studies) for homogeneous formulations of a P11/P12 blend would be conducted in a similar way to that described above, except that excess drug would be added to the glass bottles before taring and the addition of the chlorofluorocarbon components. In addition, the valves used would be non-metering continuous valves fitted with a dip tube pre-cut to position the end of the tube at the bottom of the bottle.

EXAMPLE 5

Solubilization Level Determinations

To facilitate the determination of solubilization levels, an excess amount of drug(s) was incorporated into small sections cut from a 5 ml glass serological pipette (6 mm × 2.5 cm). One end of the tube was plugged using a tight fitting glass fibre core, and, after taring in a specially constructed mounting plate, a known weight of drug was added to the tube. The other end was then similarly plugged. The bottle was prepared as described in Example 3. When filling with the P11 concentrate, care was taken to wet the tube contents as it stood on end on the base of the inclined bottle so as to prevent a sudden expansion of the contents which might result in blowing the plug out and curtailing the experiment. The use of the plugged glass tube was to prevent drug particles from contaminating the solution phase prior to assay. The glass fibre plugs, however, did not prevent contact of the drug with the liquid components of the pressurized pack and so were considered not to hinder potential solubilization of the drug.

Following an equilibrium period (up to 6 weeks), it was necessary to assay the CFC blend for the presence of solubilized drug. This was facilitated by slowly and carefully actuating the solution contents of the bottle into P113 contained in a narrow-necked round bottom flask, using an adapted actuator to which a length of neoprene tubing was attached. The spray orifice had been increased in diameter using a hand-held drill bit and the tube was introduced as a snug fit. Using this method, it was possible to empty the entire contents of the pack into the P113 reservoir.

Following complete emptying, the pack was opened using a pipe cutting tool and the inside of the bottle and outside of the glass tube were washed with further P113. The contents of the round bottomed flask were evaporated to dryness using a rotary evaporator (Büchi, Switzerland) and the film re-dissolved in a known volume of P113.

Figure 2:
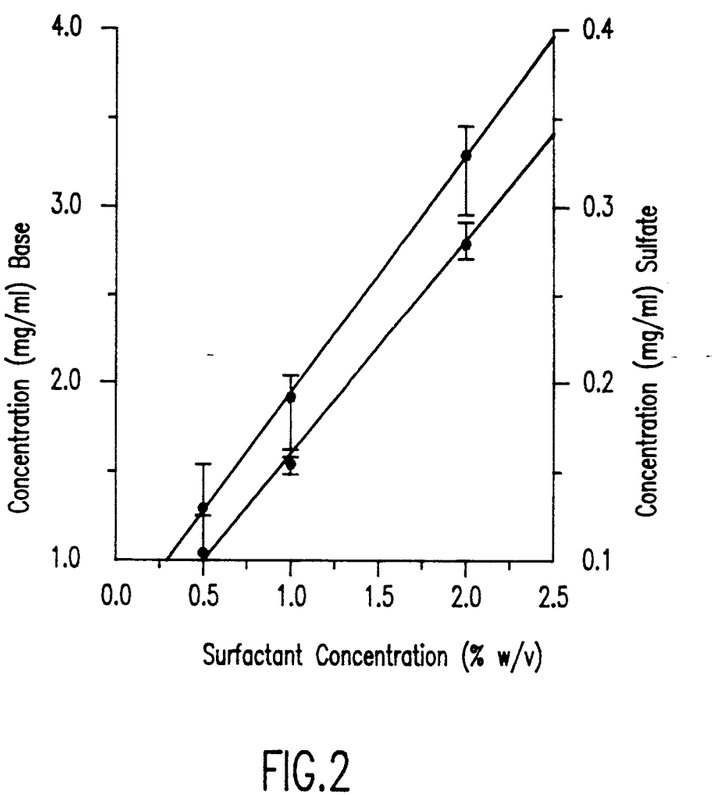
FIG. 2 is a graph showing the concentration of salbutamol in its base and salt forms which is solubilized in a CFC blend by different concentrations of surfactant.

Spectrophotometric assay of the drug contents was carried out using an UV spectrophotometer (LKB, UK) of the experimental solution against a lecithin/P113 blank at 276 nm. The concentration of drug was then related back to the original 20 ml fill of the pressure pack. The results of this assay are shown in FIG. 2.

COMPARATIVE EXAMPLE 1

Reverse Micelle Formulation With Same Strength Suspension Aerosol

In order to study the influence of drug loading on the deposition of isotropic homogeneous pressurized pack formulations, packs were manufactured by the methods outlined, with the addition of a precise weight of albuterol base, to produce a final concentration of 2.0 mg/ml. After sealing, these packs were sonicated to promote solubilization and equilibrated at 25° C. until no solid drug was present by visual examination.

Deposition studies to compare the performance of these formulations with Ventolin ® were carried out using a glass multistage liquid impinger (MLI). The deposition and valve delivery were measured by UV spectrophotometric determination, using placebo pressurized packs under the same experimental conditions as blanks for the assay.

Figure 3:
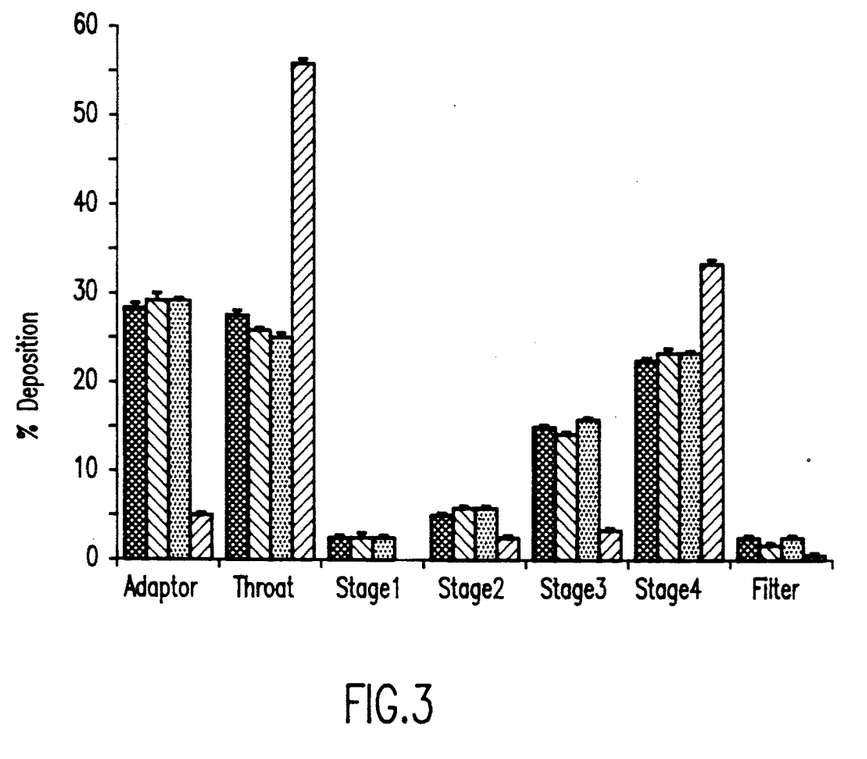
FIG. 3 is a histogram graph showing a comparison of the deposition profiles of salbutamol in a multistage liquid impinger using reverse micelle formulations of the present invention and using a commercially available suspension product.

Homogeneous systems containing albuterol base at concentrations of 0.5, 1.0 and 2.0 mg/ml were easily formulated as described in Example 3, at approximately the same vapor pressure as Ventolin ®, and showed similar deposition profiles in the MLI to one another but were considerably different from those recorded for Ventolin ® as shown in FIG. 3.

Large actuator and small throat deposition is characteristic of the homogeneous formulations while the converse is true for the suspension system (Ventolin ®). The net result is that deposition within the MLI is approximately the same for all packs, while the mass median aerodynamic diameter (MMAD) and geometric standard deviation ($\sigma g$) for Ventolin ® are smaller as shown in Table 2. The significant differences ($p<0.0001$) seen between the mean values for actuator and throat deposition for the three homogeneous and one heterogeneous (Ventolin ®) pressure packs are likely to be a result of both actuator and formulation variables.

The actuator chosen for the solution phase system had a small orifice diameter and a short orifice length, producing a wide cone with efficient disruption of the solution phase. This leads to increased actuator deposition but smaller droplets leaving the actuator and so less deposition in the throat. For suspension systems which have the same vapor pressure but a larger orifice diameter, in order to prevent clogging larger primary droplets are generated which can potentially contain more than one micronized drug particle per droplet and are deposited on the throat through impaction.

A similar fraction of each formulation entered the MLI, but differences were seen in the MMAD and $\sigma g$. Deposition for Ventolin ® aerosols probably reflects secondary droplets, each containing one particle which have evaporated to a size equivalent to the mean particle size of a drug. This constraint on final diameter would also explain smaller observed values for $\sigma g$. Homogeneous systems produce larger and more polydisperse secondary aerosol droplets due to decreased evaporation rates produced by higher surfactant concentration. Dalby and Byron (Pharm. Res., 5 (1988) 36) have shown that the oleic acid used in Ventolin ® could form a greater barrier than lecithin for evaporation but in these experiments more of the latter is present.

The results of these comparison can be seen in FIG. 3 and in Table 2.

TABLE 2

| | | DEPOSITION STUDIES USING VENTOLIN ® AND REVERSE MICELLE FORMULATIONS" | | | |
|---|---|---|---|---|---|
| | pressure pack | % entering MLI (mean ± s.d.) | RF % <5 μm (mean ± s.d.) | MMAD (μM) | mg of drug delivered |
| Ex. 6 | 0.5 mg/ml | 45.06 ± 1.58 | 37.54 ± 1.09 | 3.47 | 0.009 |
| Ex. 7 | 1.0 mg/ml | 45.55 ± 2.38 | 37.50 ± 1.44 | 3.54 | 0.019 |
| Ex. 8 | 2.0 mg/ml | 46.35 ± 1.40 | 38.40 ± 0.82 | 3.51 | 0.038 |
| Comp. Ex. 1 | Ventolin | 39.21 ± 1.59 | 36.77 ± 1.41 | 3.03 | 0.037 |

What is claimed is:

1. A method of preparing an aerosol formulation for drug delivery to a patient's lungs, comprising the steps of:

drying a surfactant from which reverse micelles can be formed; and mixing said surfactant with a drug, an amount of water, and a propellant to form reverse micelles of said surfactant in said propellant which incorporate said drug, said surfactant being present in an amount ranging from 0.025 to 2.5 percent weight in volume, said drug being present in an amount less than 10 percent by weight, said propellant being present in an amount of at least 90 percent by weight, and said amount of water resulting in a molar ratio of water to surfactant ranging from approximately 1:1 to 20:1.

2. A method as recited in claim 1 wherein said drying step reduces an amount of associated water from said surfactant to yield a molar ratio of associated water to surfactant ranging from 0.5:1 to 1:1.

3. A method as recited in claim 1 wherein said amount of water in said mixing step results in a molar ratio of water to surfactant of 1:1 to 5:1.

4. A method as recited in claim 1 wherein said amount of water in said mixing step forms reverse micelles of prolate shape.

5. A method as recited in claim 1 wherein said amount of water in said mixing step forms reverse micelles of oblate shape.

6. A method as recited in claim 1 wherein said amount of water in said mixing step forms reverse micelles of spherical shape.

7. A method of preparing an aerosol formulation of salbutamol for delivery to a patient's lungs, comprising the steps of:

drying a surfactant from which reverse micelles can be formed;

mixing said surfactant with salbutamol in its base or salt form, an amount of water, and a propellant to form reverse micelles of said surfactant in said propellant which incorporate said salbutamol, said surfactant being present in an amount ranging from 0.05 to 2.5 percent weight in volume, said salbutamol being present in an amount less than 10 percent by weight, said propellant being present in an amount of at least 90 percent by weight, and said amount of water resulting in a molar ratio of water to surfactant ranging from approximately 1:1 to 20:1.

8. A method as recited in claim 1 wherein said amount of water used in said mixing step results in a molar ratio of water to surfactant being 2:1 or less for salbutamol in its base form.

9. A method as recited in claim 1 wherein said amount of water used in said mixing step results in a molar ratio of water to surfactant being 2:1 or more for salbutamol in its salt form.

10. A method of preparing an aerosol formulation for drug delivery to a patient's lungs, comprising the steps of:

combining a surfactant with a drug and a propellant, said surfactant being present in an amount ranging from 0.05 to 2.5 percent weight in volume, said drug being present in an amount less than 10 percent by weight, and said propellant being present in an amount of at least 90 percent by weight; and adjusting an amount of water associated with said surfactant to solubilize said drug in reverse micelles formed from said surfactant and dispersed within said propellant, said amount of water being adjusted to a molar ratio of water to surfactant of up to 20:1.

11. A method as recited in claim 10 wherein said step of adjusting yields reverse micelles that have a prolate shape.

12. A method as recited in claim 10 wherein said step of adjusting yields reverse micelles that have an oblate shape.

13. A method as recited in claim 10 wherein said step of adjusting yields reverse micelles that have a spherical shape.

14. A method of preparing an aerosol formulation for drug delivery to a patient's lungs, comprising the steps of:

drying a surfactant from which reverse micelles can be formed; and mixing said surfactant with a drug, an amount of water, and a propellant to form reverse micelles of said surfactant in said propellant which incorporate said drug, said surfactant being present in an amount ranging from 0.05 to 2.5 percent weight in volume, said drug having a concentration in said propellant ranging from 0.025 mg/ml to 4.0 mg/ml, and said amount of water resulting in a molar ratio of water to surfactant ranging from approximately 1:1 to 20:1.

15. A method as recited in claim 14 wherein said drying step reduces an amount of associated water from said surfactant to yield a molar ratio of associated water to surfactant ranging from 0.5:1 to 1:1.

16. A method as recited in claim 14 wherein said amount of water in said mixing step results in a molar ratio of water to surfactant of 1:1 to 5:1.

17. A method as recited in claim 14 wherein said amount of water in said mixing step forms reverse micelles of prolate shape.

18. A method as recited in claim 14 wherein said amount of water in said mixing step forms reverse micelles of oblate shape.

19. A method as recited in claim 14 wherein said amount of water in said mixing step forms reverse micelles of spherical shape.

20. A method as recited in claim 14 wherein said propellant includes a gas selected from the group consisting of n-butane, isobutane, perfluoropentane, triclorofluoromethane, dichlorotetrafluoroethane, dichlorofluoroethane, dichlorodifluoromethane, 1,1,1,2-tetrafluoroethane, propane, dimethylether, perfluoropropane, and heptafluoropropane.

21. A method as recited in claim 14 wherein said surfactant is selected form the group consisting of phosphatidyl choline, phosphatidyl ethanolamine, phosphatidyl inositol, phosphatidyl serine, diphosphatidyl glycerol, sorbitan mono- and tri-oleates, diolein, oleic acid, and phosphatidic acid.

22. A method as recited in claim 14 wherein said drug is selected from group consisting of steroids, anorectics, peptides, anti-depressants, anti-hypertensive agents, anti-neoplastic agents, anti-cholinergic agents, dopaminergic agents, narcotic analgesics, beta-adrenergic blocking agents, corticosteroids, prostaglandins, sympathomimetics, tranquilizers, vitamins, bronchodilaters, sex hormones, and pharmaceutically active salts, alcohols, and esters thereof.

23. A method of preparing an aerosol formulation for drug delivery to a patient's lungs, comprising the steps of:

combining a surfactant with a drug and a propellant, said surfactant being present in an amount ranging from 0.05 to 2.5 percent weight in volume, said drug having a concentration in said propellant ranging from 0.025 mg/ml to 4.0 mg/ml; and adjusting an amount of water associated with said surfactant to solubilize said drug in reverse micelles formed from said surfactant and dispersed within said propellent, said amount of water being adjusting to a molar ratio of water to surfactant of up to 20:1.

24. A method as recited in claim 1 wherein said propellant includes a gas selected from the group consisting of n-butane, isobutane, perfluoropentane, trichlorofluoromethane, dichlorotetrafluoroethane, dichlorofluoroethane, dichlorodifluoromethane, 1,1,1,2 tetrafluoroethane, propane, dimethylether, perfluoropropane and heptafluoropropane.

25. A method as recited in claim 1 wherein said surfactant is selected from the group consisting of phosphatidyl choline, phosphatidyl ethanolamine, phosphatidyl inositol, phosphatidyl serine, diphosphatidyl glycerol, sorbitan mono- and tri-oleates, diolein, oleic acid and phosphatidic acid.

26. A method as recited in claim 1 wherein said drug is selected from the group consisting of steroids, anorectics, peptides, anti-depressants, anti-hypertensive agents, anti-neoplastic agents, anti-cholinergic agents, dopaminergic agents, narcotic analgesics, beta-adrenergic blocking agents, corticosteroids, prostaglandins, sympathomimetics, tranquilizers, vitamins, brochodilators, sex hormones, and pharmaceutically active salts, alcohols, and esters thereof.

27. A method as recited in claim 1 wherein said step of drying is accomplished by freeze drying said surfactant.

28. A method as recited in claim 1 wherein said step of drying is accomplished by heating said surfactant.

29. A method as recited in claim 1 wherein said step of drying includes the step of washing said surfactant with a heated organic alcohol.

30. A method as recited in claim 29 wherein said organic alcohol is methanol.

31. A method as recited in claim 1 further comprising the step of purifying said surfactant.

* * * * *